United States Patent [19]

Haslam et al.

[11] Patent Number: 4,886,668
[45] Date of Patent: Dec. 12, 1989

[54] MULTIPARTICULATE CONTROLLED POROSITY OSMOTIC PUMP

[75] Inventors: John L. Haslam; Gerald S. Rork, both of Lawrence, Kans.

[73] Assignee: Merck & Co., Inc., Rahway, N.J.

[21] Appl. No.: 100,676

[22] Filed: Sep. 24, 1987

[51] Int. Cl.$^4$ ............................................. A61K 31/55
[52] U.S. Cl. ..................................... 424/424; 424/426; 424/457; 424/468; 424/472
[58] Field of Search ........ 424/468, 424, 426, 457–462, 424/469

[56] References Cited

U.S. PATENT DOCUMENTS

| | | |
|---|---|---|
| 3,538,214 | 11/1970 | Polli et al. . |
| 3,845,770 | 11/1974 | Theeuwes et al. . |
| 3,916,899 | 11/1975 | Theeuwes et al. . |
| 3,957,523 | 5/1976 | Ohno et al. . |
| 4,160,452 | 7/1979 | Theeuwes . |
| 4,200,098 | 4/1980 | Ayer et al. . |
| 4,244,941 | 1/1981 | Lerk . |
| 4,256,108 | 3/1981 | Theeuwes . |
| 4,285,987 | 8/1981 | Ayer et al. . |
| 4,326,525 | 4/1982 | Swanson et al. . |
| 4,578,075 | 3/1986 | Urquhart et al. ................. 424/453 |
| 4,696,924 | 9/1987 | Marcoux .......................... 514/211 |
| 4,747,845 | 5/1988 | Korol .............................. 424/443 |

OTHER PUBLICATIONS

Jm Pharm. Sci. 72, 772–775.

*Primary Examiner*—Nancy A. B. Swisher
*Attorney, Agent, or Firm*—Joseph F. DiPrima; Michael C. Sudol, Jr.

[57] ABSTRACT

The instant invention is directed to a multiparticulate osmotic pump, for the controlled release of diltiazem L-malate to an environment of use, said pump comprising:
(I) a carrier medium which does not maintain its integrity in the environment of use;
(II) a multiple of tiny osmotic pump elements each comprising:
(A) a core comprises diltiazem L-malate and an effective buffering amount of sodium bitartrate surrounded by
(B) a rate controlling water insoluble wall, having a fluid permeability of $6.96 \times 10^{-18}$ to $6.96 \times 10^{-14}$ cm$^3$ sec/g and a reflection coefficient of less than 0.5, prepared from:
   (i) a polymer permeable to water but impermeable to solute and
   (ii) 0.1 to 60% by weight, based on the total weight of (i) and (ii), of at least one pH insensitive pore forming additive dispersed throughout said wall,
wherein the total amount of diltiazem L-malate in all of the osmotic pump elements is a therapeutically effective amount.

22 Claims, 4 Drawing Sheets

4,886,668

MULTIPARTICULATE CONTROLLED POROSITY OSMOTIC PUMP

BACKGROUND OF THE INVENTION

Diltiazem hydrochloride is a calcium ion influx inhibitor which is commercially utilized in the treatment of angina pectoris due to coronary artery spasm and chronic stable angina.

Controlled delivery devices for therapeutically active agents are well known in the art. Generally, these devices may be characterized as either diffusion controlled delivery systems or osmotic dispensing devices. U.S. Pat. No. 3,538,214 discloses a diffusion controlled device in which a tablet core containing an active ingredient is surrounded by a water insoluble coating which contains film modifying agent soluble in the external fluids in the gastrointestinal tract. An example of an osmotic device is described in U.S. Pat. Nos. 3,845,770 and 3,916,899 which is a core composition of an active agent and an osmotically effective solute which is enclosed by an insoluble semipermeable wall having a release means. Numerous modifications to these types of delivery devices have been described in the art in an effort to improve their release characteristics.

The use of pore formers in substantially water impermeable polymers, such as polyvinyl chloride, is disclosed in J. Pharm. Sci. 72, 772–775 and U.S. Pat. No. 4,244,941. The devices release the core contents by simple diffusion through the pores in the coating.

U.S. Pat. No. 3,957,523 discloses a device which has pH sensitive pore formers in the wall.

U.S. Pat. Nos. 4,256,108; 4,160,452; 4,200,098 and 4,285,987 disclose devices with pore formers in only one of at least two wall layers. These devices contain a drilled hole for the release of the core contents.

Co-pending U.S. Pat. applications Ser. Nos. 073781 and 073596 disclose systems which comprise an inner core compartment of osmotically active composition surrounded by an enclosing controlled porosity wall material that is substantially permeable to both solute and external fluid. These systems are osmotic dispensing devices for a broad range of therapeutically active agents. However, the delivery of a highly soluble agent from these devices at a constant rate is difficult to achieve.

U.S. Pat. No. 4,326,525 addresses the problem of delivering an active agent from an osmotic device by incorporating into the core a buffer which enters into a proton transfer or neutralization reaction with the agent thereby producing an aqueous soluble agent salt within the device.

BRIEF DESCRIPTION OF THE INVENTION

This invention concerns an osmotically activated system for dispensing diltiazem L-malate, as the pharmacologically active agent, to biological receptor sites over a prolonged period of time. The system comprises an inner core compartment of osmotically active composition surrounded by an enclosing wall material. The core comprises diltiazem L-malate and sodium bitartrate, which exhibit unique solublity characteristics in an external fluid, and an osmotic pressure gradient across the wall against the external fluid. The wall constitutes a layer of controlled porosity that is substantially permeable to both the external fluid and the aqueous solution of the core composition. Diltiazem L-malate and sodium bitartrate are released from the system in a pH independent manner by external fluid imbibition through the wall into the inner core compartment at a rate controlled by the wall composition and dimensions, producing a solution containing core composition that is released through the wall at a controlled rate in response to fluid volume flux, dV/dt, resulting from the osmotic pressure gradient, and diffusive flux, $(dM/dt)_D$, driven by the chemical potential gradient of the core composition across the wall. The total rate of release, $(dM/dt)_T$, is given by Equation 1 where C $$\left(\frac{dM}{dt}\right)_T = \frac{dV}{dt}(C) + \left(\frac{dM}{dt}\right)_D \qquad \text{Eq. 1}$$

is the concentration of the active agent in the dissolved core composition and remains constant when excess solid core mass is present. In the present invention the volume flux contribution, $(dV/dt)C$, to the total rate is expected to be greater than the diffusive contribution, $(dM/dt)_D$, add forms the basis for the osmotic pump action of the device.

The present invention include osmotic systems that are readily manufactureable to deliver a pre determined dose of agent at a programmed rate from compositions of matter in the varied geometries and sizes of tablets, pellets, multi-particulates, and such related dosage forms as familiar to those skilled in the art for oral, buccal, vaginal, rectal, nasal, ocular, parenteral and related routes of administration. The invention also provides osmotic systems that deliver agent on an equivalent mass per unit surface area basis.

A BRIEF DESCRIPTION OF THE DRAWINGS

FIG. 1 is an embodiment of the osmotic pump element (1), having an osmotically active core composition (3) comprised of diltiazem L-malate, as the active agent and sodium bitartrate alone or admixed with other inert pharmaceutically acceptable carriers.

FIG. 2 shows embodiments of multiparticular osmotic pumps (2a and 2b) in a solid carrier medium (7) and a hollow carrier medium (9). Both embodiments contain multiple pump elements (1) as detailed in FIG. 1. The embodiments can be distinguished by the solid matrix (6) of embodiment (7) and the hollow spaces (8) of embodiment (9) which are formed by those areas of the carrier medium not occupied by the osmotic pump elements (1).

DETAILED DESCRIPTION OF THE INVENTION

The instant invention is directed to a multiparticulate osmotic pump, for the controlled release of diltiazem L-malate to an environment of use, said pump comprising:

(I) a carrier medium which does not maintain its integrity in the environment of use;

(II) a multiple of tiny osmotic pump elements each comprising:

(A) a core which comprises diltiazem L malate and an effective buffering amount of sodium bitartrate surrounded by (B) a rate controlling water insoluble wall, having a fluid permeability of $6.96 \times 10^{-18}$ to $6.96 \times 10^{-14} cm^3$ sec/g and a reflection coefficient of less than 0.5, prepared from:
  (i) a polymer permeable to water but impermeable to solute and
  (ii) 0.1 to 60% by weight, based on the total weight of (i) and (ii), of at least one pH insensitive pore forming additive dispersed throughout said wall, wherein the total amount of diltiazem L malate in all of the osmotic pump elements is a therapeutically effective amount.

Figure 1:
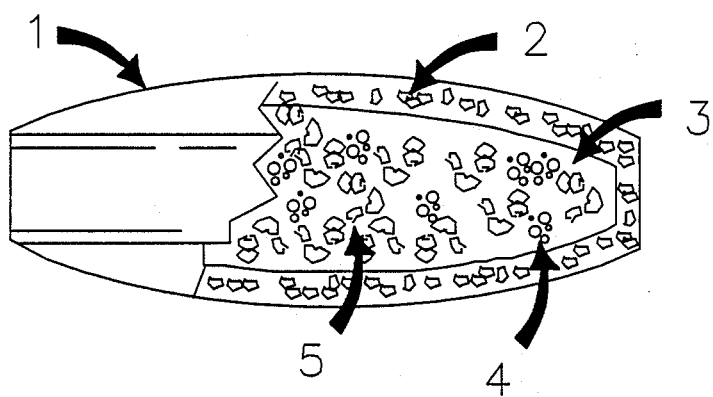

The osmotically active core composition mass (3) of FIG. 1, is typically a pellet, or multiparticulate. The core is completely encased by the controlled porosity wall (2). The core is comprised of a mixture of diltiazem L malate and sodium bitartrate, as well as other inert pharmaceutically acceptable carriers, which are not osmotically effective agents (4, 5, etc.) combined to give the desired manufacturing and ultimate delivery characteristics.

The preferred specifications for the core are summarized below and include:

| | | |
|---|---|---|
| 1. | Size of Multiparticulate | 0.1 millimeter to 5 millimeters or larger |
| 2. | Total Core Loading (Size) | 0.1 milligrams to 5 grams or more (includes dosage forms for humans and animals) |
| 3. | Core solubility | to get continuous, uniform release (zero-order kinetics) of 50% or greater of the initially loaded core mass, the ratio of the core mass solubility, S, to the core mass density, $\rho$, that is $S/\rho$, must be 0.5 or lower. Typically this occurs when 50% of the initially loaded core mass saturates a volume of external fluid equal to the total volume of the initial core mass. |

$S/\rho$ ratios less than 0.5 fall within the workings of the invention and result in higher percentages of initial core mass delivered under zero-order kinetics. $S/\rho$ can be selected to give acceptable combined characteristics of stability, release rate, and manufacturability.

In the present invention diltiazem L malate, as the active agent, when combined with an effective buffering amount of sodium bitartrate has the desired solubility, osmotic pressure, density, stability, and manufacturability characteristics. The effective buffering amount of sodium bitartrate is an amount sufficient to hold the pH of the osmotic pump constant in the range of 3 to 4 and does not form a salt with diltiazem. Between about 80 and 150 percent by weight of sodium bitartrate has been found to be sufficient as an effective buffering amount.

There is no critical upper limit as to the amount that can be incorporated into a core mass and typically will follow the core loading (size) specification 1. However, the maximum amount of diltiazem L malate contained in the total core compositon of the multiparticulates should not exceed the amount which is necessary to deliver the equivalent amount of diltiazem hydrochloride recommended for approved therapeutic uses. The lower limit ratio of diltiazem L-malate and sodium bitartrate to other inert pharmaceutically acceptable carriers is dictated by the pharmacological activity of the active agent. Generally the core will contain 0.01% to 90% by weight or higher, of diltiazem L-malate, as the active agent and sodium bitartrate in mixture with other inert pharmaceutically acceptable carriers. The solubilized constituents create a water activity gradient across the wall, (2), of FIG. 1, resulting in osmotically actuated fluid movement constituting the osmotic pump action of the invention.

The amount of diltiazem L-malate, as the active agent and sodium bitartrate alone or admixed with other inert pharmaceutically acceptable carriers present in the device is initially in excess of the amount that can be dissolved in the fluid that enters the reservoir. Under this physical state when the agent is in excess, the device will osmotically operate to give a substantially constant rate of release. The rate of agent release pattern can also be varied by having different amounts of agent in the reservoir to form solutions containing different concentrations of agent for delivery from the device. Generally, the carrier medium can house from 0.1 mg to 5 grams or more, with individual devices containing, for example, 1 mg, 5 mg, 25 mg, 50 mg, and the like.

As a specific embodiment of the present invention, the total amount of diltiazem L malate in the core of all the osmotic pump elements is between 30 and 500 mg and as another specific embodiment of the present invention, the total amount of sodium bitartrate both in the core of all the osmotic pump elements is between 30 and 500 mg.

The resulting device will have a water permeability driven by a saturated solution of diltiazem L-malate, as the active agent and sodium bitartrate at the temperature of use, of 0.01 ml per $cm^2$ of surface area per day to 10 ml per $cm^2$ of surface area per hour.

The controlled porosity wall of the present invention is substantially permeable to both solute and external fluid. The wall is composed of materials that maintain their physical and chemical integrity during the controlled dispensing of agent in mixture with materials that can be leached into the external fluid. The wall has programmable fluid transmission rate which provide for controlled release of agent which is nearly free from environmental influences including pH and degree of external fluid agitation.

The wall may be composed of either insoluble, nonerodible materials mixed with leachable additives, or bioerodible materials containing leachable additives. Bioerodible materials would be selected to bioerode after a predetermined period with bioerosion occurring subsequent to the period of agent release.

The phrase "permeable to water but impermeable to solutes" means the water permeates through the polymer preferably to solute, under a pressure differential.

Figure 2:
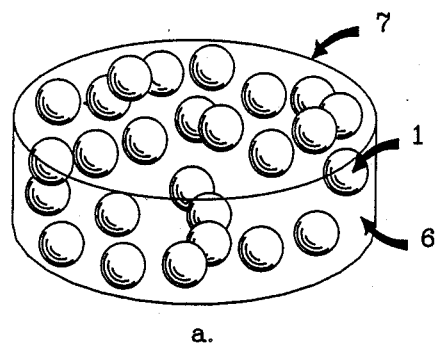
Figure 2:
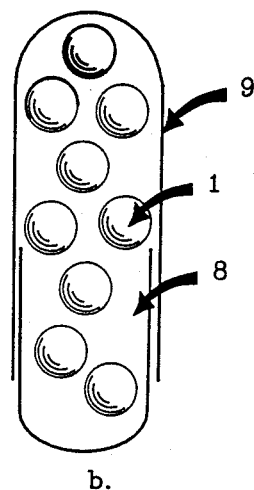

Referring to FIG. 2, each osmotic pump element is typically in the form of coated pellets, beads and multiparticulates having the essential features and elements of FIG. 1, of a size such that several such devices may be loaded into solid carrier media, such as a soluble gelatin capsule or tablet matrix for oral administrations or suspended in a suitable fluid carrier media for injection, oral administration or spraying. Whether solid or fluid, the carrier media become disrupted in the environment of use, thereby freeing the osmotic pump elements to release the active agent at a predetermined controlled rate.

The water insoluble, permeable wall (2) of controlled porosity may be applied to osmotically active core composition masses (3) by spray coating procedures. The wall is comprised of (a) polymeric material that is insoluble in the fluids of the environment of intended use (usually water); (b) other added excipients that will dissolve in the environmental fluids and leach out of the wall. The leached wall is a sponge-like structure composed of numerous open and closed cells that form a discontinuous interwoven network of void spaces when viewed with a scanning electron microscope. This controlled porosity wall serves as both the water entry and core composition solution exit sites. The wall is permeable to both water and solutes, and as constituted in the environment of use has a small solute reflection coefficient, o, and displays poor semipermeable characteristics when placed in a standard osmosis cell. The specifications for the wall are summarized below and include:

| 1. | Fluid Permeability of the wall | $6.96 \times 10^{-18}$ to $6.96 \times 10^{-14}$ cm$^3$ sec/g (equivalent to $10^{-5}$ to $10^{-1}$ cm$^3$mil/cm$^2$ hr atm) |
|---|---|---|
| 2. | Reflection Coefficient | Microporous coats to have a reflection coefficient, $\sigma$, defined as: hydrostatic pressure difference $$\sigma = \frac{\text{x osmotic volume flux}}{\text{osmotic pressure difference}}$$ x hydrostatic volume flux where $\sigma$ is less than 1, usually 0 to 0.8. |

A specific embodiment of the present invention are those osmotic pumps wherein the reflection coefficient of the wall is less than 0.5. Exemplifying this embodiment are those osmotic pumps wherein the reflection coefficient of the wall is less than 0.1.

Additional, preferred specifications for the wall include:

| 1. | Plasticizer and Flux Regulating Additives | 0 to 50, preferably 0.001 to 50, parts per 100 parts wall material |
|---|---|---|
| 2. | Surfactant Additives | 0 to 40, preferably .001 to 40, parts per 100 parts wall material |
| 3. | Wall Thickness | 1 to 1,000, preferably 10 to 100, microns typically although thinner and thicker fall within the invention |
| 4. | Microporous Nature | 5% to 95% pores between 10 angstroms and 100 microns diameter |
| 5. | Pore forming Additives | 0.1 to 60%, preferably 0.1 to 50%, by weight, based on the total weight of pore forming additive and polymer, pH insensitive pore forming additive, preferably: (a) 0.1 to 50%, preferably 0.1 to 40% by weight solid additive (b) 0.1 to 40% by weight liquid additive But no more than 60% total pore formers. |

The water insoluble wall of the instant invention must not be covered on its inner or outer surface by a layer of material that is impermeable to dissolved solutes within the core during the period of pumping operation.

Any polymer film by itself permeable to water but impermeable to solutes as previously defined may be used. However, the polymer film may be covered initially by a rapid dissolving coat used for aesthetic purposes or containing a second drug substance. Examples include cellulose acetate having a degree of substitution, D.S., meaning the average number of hydroxyl groups on the anhydroglucose unit of the polymer replaced by a substituting group, up to 1 and acetyl content up to 21%; cellulose diacetate having a D.S. of 1 to 2 and an acetyl content of 21 to 35%; cellulose triacetate having a D.S. of 2 to 3 and an acetyl content of 35 and 44.8%; cellulose propionate having an acetyl content of 1.5 to 7% and a propionyl content of 2.5 to 3% and an average combined propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acetate having an acetyl content of 2 to 99.5%, a butyryl content of 17 to 53%, and a hydroxyl content of 0.5 to 4.7%; cellulose triaceylates having a D.S. of 2.9 to 3 such as cellulose trivalerate, cellulose trilaurate, cellulose tripalmitate, cellulose trisuccinate, cellulose triheptylate, cellulose tricaprylate, cellulose trioctanoate, and cellulose tripropionate; cellulose diesters having a lower degree of substitution and prepared by the hydrolysis of the corresponding triester to yield cellulose diacylates having a D.S. of 2.2 to 2.6 such as cellulose dicaprylate and cellulose dipentanate; and esters prepared from acyl anhydrides or acyl acids in an esterification reaction to yield esters containing different acyl groups attached to the same cellulose polymer such as cellulose acetate valerate, cellulose acetate succinate, cellulose propionate succinate, cellulose acetate octanoate, cellulose valerate palmitate, cellulose acetate palmitate and cellulose acetate heptanoate.

Additional polymers that can be used for the purpose of the invention include cellulose acetate acetoacetate, cellulose acetate chloroacetate, cellulose acetate furoate, dimethoxyethyl cellulose acetate, cellulose acetate carboxymethoxypropionate, cellulose acetate benzoate, cellulose butyrate naphthylate, cellulose acetate benzoate, methylcellulose acetate methylcyanoethyl cellulose, cellulose acetate methoxyacetate, cellulose acetate ethoxyacetate, cellulose acetate dimethylsulfamate, ethylcellulose, ethylcellulose dimethylsulfamate, cellulose acetate p-toluene sulfonate, cellulose acetate methylsulfonate, cellulose acetate dipropylsulfamate, cellulose acetate butylsulfonate, cellulose acetate laurate, cellulose stearate, cellulose acetate methylcarbamate, agar acetate, amylose triacetate beta glucan acetate, beta glucan triacetate, acetaldehyde dimethyl acetate, cellulose acetate ethyl carbamate, cellulose acetate phthalate, cellulose acetate dimethyl aminoacetate, cellulose acetate ethyl carbonate, poly (vinyl methyl) ether copolymers, cellulose acetate with acetylated hydroxyethyl cellulose hydroxylated ethylenevinylacetate, poly (ortho ester)s, polyacetals, semipermeable polyglycolic or polylactic acid and derivatives thereof, selectively permeable associated polyelectrolytes, polymers of acrylic and methacrylic acid and esters thereof, film forming materials with a water sorption of one to fifty percent by weight at ambient temperatures with a presently preferred water sorption of less than thirty percent, acylated polysaccharides, acylated starches, aromatic nitrogen containing polymeric materials that exhibit permeability to aqueous fluids, membranes made from polymeric epoxides, copolymers of alkylene oxides and alkyl glycidyl ethers, polyurethanes, and the like. Admixtures of various polymers may also be used.

The polymers described are known to the art or they can be prepared according to the procedures in *Encyclopedia of Polymer Science and Technology*, Vol. 3, pages 325 to 354, and 459 to 549, published by Interscience Publishers, Inc., N.Y., in *Handbook of Common Polymers* by Scott, J. R. and Roff, W. J., 1971, published by CRC Press, Cleveland, Ohio; and in U.S. Pat. Nos. 3,133,132; 3,173,876; 3,276,586; 3,541,055; 3,541,006; and 3,546,142.

A controlled porosity wall can be generically described as having a sponge like appearance. The pores can be continuous pores that have an opening on both faces of a microporous lamina, pores interconnected through tortuous paths of regular and irregular shapes including curved, curved-linear, randomly oriented cOntinuous pores, hindered connected pores and other porous paths discernible by microscopic examination. Generally, microporous lamina are defined by the pore size, the number of pores, the tortuosity of the microporous path and the porosity which relates to the size and number of pores. The pore size of a microporous lamina is easily ascertained by measuring the observed pore diameter at the surface of the material under the electron microscope. Generally, materials possessing from 5% to 95% pores and having a pore size of from 10 angstroms to 100 microns can be used.

Any pH insensitive pore forming additives may be used in the instant invention. The microporous wall may be formed in situ, by a pore-former being removed by dissolving or leaching it to form the microporous wall during the operation of the system The pores may also be formed in the wall prior to operation of the system by gas formation within curing polymer solutions which result in voids and pores in the final form of the wall. The pore-former can be a solid or a liquid. The term liquid, for this invention embraces semi-solids, and viscous fluids. The pore-formers can be inorganic or organic. The pore-formers suitable for the invention include pore-formers than can be extracted without any chemical change in the polymer. Solid additives include alkali metal salts such as sodium chloride, sodium bromide, potassium chloride, potassium sulfate, potassium phosphate, sodium benzoate, sodium acetate, sodium citrate, potassium nitrate and the like. The alkaline earth metal salts such as calcium chloride, calcium nitrate, and the like. The transition metal salts such as ferric chloride, ferrous sulfate, zinc sulfate, cupric chloride, and the like. Water may be used as the pore former. The pore-formers include organic compounds such as saccharides. The saccharides include the sugars sucrose, glucose, fructose, mannose, galactose, aldohexose, altrose, talose, lactose, monosaccharides, disaccharides, and water soluble polysaccharides Also, sorbitol, mannitol, organic aliphatic and aromatic ols, including diols and polyols, as exemplified by polyhydric alcohols, poly(alkylene glycols), polyglycols, alkylene glycols, poly($\alpha,\omega$)alkylenediols esters or alkylene glycols poly vinylalcohol, poly vinyl pyrrolidone, and water soluble materials. Pores may also be formed in the wall by the volatilization of components in a polymer solution or by chemical reactions in a polymer solution which evolves gases prior to application or during application of the solution to the core mass resulting in the creation of polymer foams serving as the porous wall of the invention. The pore formers are nontoxic, and on their removal channels are formed that fill with fluid. The channels become a transport path for fluid. In a preferred embodiment, the non-toxic pore forming agents are selected from the group consisting of inorganic and organic salts, carbohydrates, polyalkylene glycols, poly($\alpha,\omega$) alkylenediols, esters of alkylene glycols, and glycols, that are used in a biological environment.

The microporous materials can be made by etched nuclear tracking, by cooling a solution of flowable polymer below the freezing point with subsequent evaporation of solvent to form pores, by gas formation in a polymer solution which upon curing results in pore formation, by cold or hot stretching at low or high temperatures until pores are formed, by leaching from a polymer a soluble component by an appropriate solvent, by ion exchange reaction, and by polyelectrolyte processes. Processes for preparing microporous materials are described in *Synthetic Polymer Membranes*, by R. E. Kesting, Chapters 4 and 5, 1971, published by McGraw Hill, Inc.; *Chemical Reviews*, Ultrafiltration, Vol. 18, pages 373 to 455, 1934; *Polymer Eng. and Sci.*, Vol. 11, No. 4, pages 284 to 288, 1971; *J. Appl. Poly. Sci.*, Vol. 15, pages 811 to 829, 1971; and in U.S. Pat. Nos. 3,565,259; 3,615,024; 3,751,536; 3,801,692; 3,852,224; and 3,849,528.

It is generally desirable from a preparation standpoint to mix the polymer in a solvent. Exemplary solvents suitable for manufacturing the wall of the osmotic device include inert inorganic and organic solvents that do not adversely harm the core, wall, and the materials forming the final wall. The solvents broadly include members selected from the group consisting of aqueous solvents, alcohols, ketones, esters, ethers, aliphatic hydrocarbons, halogenated solvents, cycloaliphatic, aromatics, heterocyclic solvents and mixtures thereof.

Exemplary plasticizers suitable for the present purpose include plasticizers that lower the temperature of the second-order phase transition of the wall or the elastic modulus thereof; and also increase the workability of the wall, its flexibility and its permeability to fluid. Plasticizers operable for the present purpose include both cyclic plasticizers and acyclic plasticizers. Typical plasticizers are those selected from the group consisting of phthalates, phosphates, citrates, adipates,tartrates, sebacates, succinates, glycolates, glycerolates, benzoates, myristates, sulfonamides, and halogenated phenyls. Generally, from 0.001 to 50 parts of a plasticizer or a mixture of plasticizers are incorporated into 100 parts of wall forming material.

Suitable plasticizers can be selected for blending with the wall forming materials by selecting plasticizers that have a high degree of solvent power for the materials, are compatible with the materials over both the processing and use temperature range, exhibit permanence as seen by their strong tendency to remain in the plasticized wall, impart flexibility to the material and are non-toxic to animals, humans, avians, fishes and reptiles. Procedures for selecting a plasticizer having the described characteristics are disclosed in the *Encyclopedia of Polymer Science and Technology*, Vol. 10, pages 228 to 306, 1969, published by John Wiley & Sons, Inc. Also, a detailed description pertaining to the measurement of plasticizer properties including solvent parameters and compatibility such as the Hildebrand solubility parameter, the Flory-Huggins interaction parameter X, and the cohesive-energy density, CED, parameters are disclosed in *Plasticization and Plasticizer Processes*, Advances in Chemistry Series 48, Chapter 1, pages 1 to 26, 1965, published by the American Chemical Society. The amount of plasticizer added generally is an amount sufficient to produce the desired wall and it will vary according to the plasticizer and the materials. Usually about 0.001 part up to 50 parts of plasticizer can be used for 100 parts of wall material.

The expressions "flux regulator agent", "flux enhancing agent" and "flux decreasing agent" as used herein mean a compound that when added to a wall forming material assists in regulating the fluid permeability of flux through the wall. The agent can be preselected to increase or decrease the liquid flux. Agents that produce a marked increase in permeability to fluid such as water, are often essentially hydrophilic, while those that produce a marked decrease to fluids such as water, are essentially hydrophobic. The flux regulators in some embodiments also can increase the flexibility and porosity of the lamina. Examples of flux regulators include polyhydric alcohols and derivatives thereof, such as polyalkylene glycols of the formula $H\text{-}(O\text{-alkylene})_n\text{-}OH$ wherein the bivalent alkylene radical is straight or branched chain and has from 1 to 10 carbon atoms and n is 1 to 500 or higher. Typical glycols include polyethylene glycols 300, 400, 600, 1500, 1540, 4000 and 6000 of the formula $H\text{-}(OCH_2CH_2)_n\text{-}OH$ wherein n is respectively 5 to 5.7, 8.2 to 9.1, 12.5 to 13.9, 29 to 36, 29.8 to 37, 68 to 84, and 158 to 204. Other polyglycols include the low molecular weight glycols such as polypropylene, polybutylene and polyamylene.

The amount of flux regulator added to a material generally is an amount sufficient to produce the desired permeability, and it will vary according to the lamina forming material and the flux regulator used to modulate the permeability. Usually from 0.001 parts up to 50 parts, or higher of flux regulator can be used to achieve the desired results.

Figure 3:
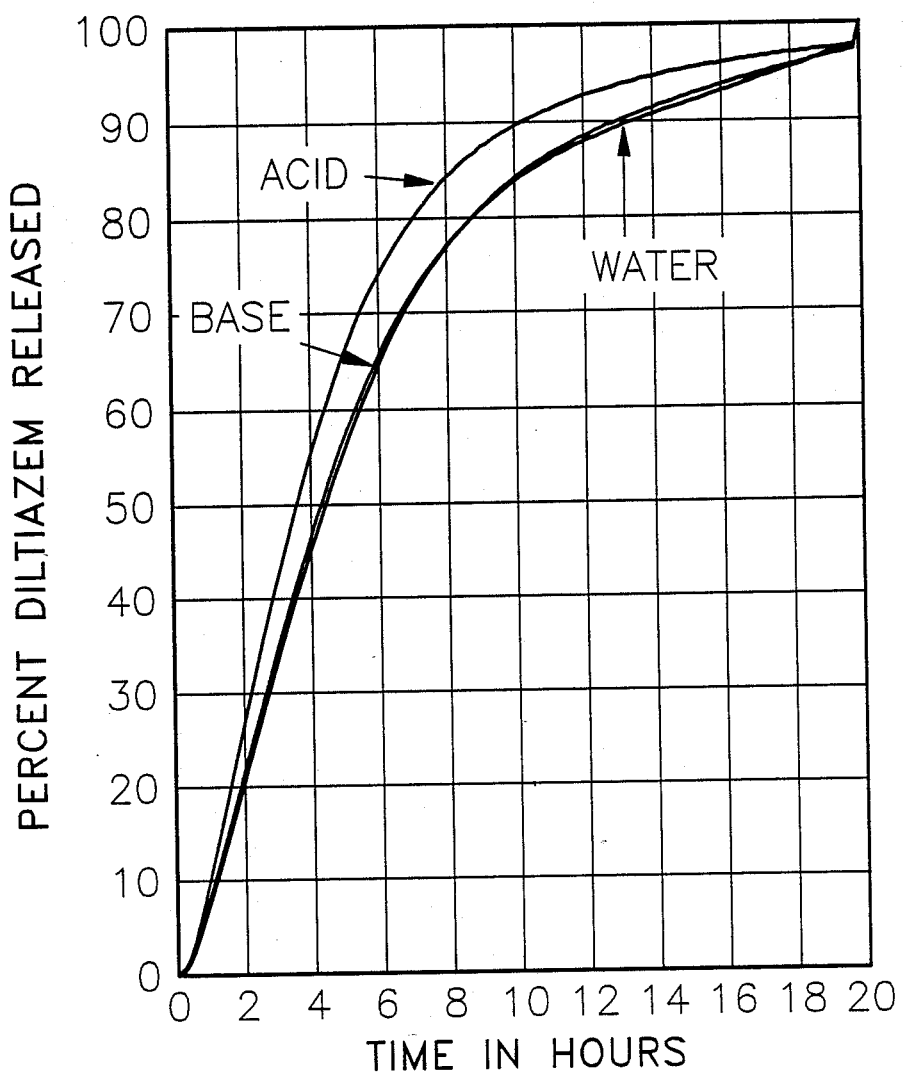
FIG. 3 is the release profile (statistical average of many pumps) of the pumps produced in Example 1.

Surfactants useful for the present purpose are those surfactants, when added to a wall forming material and other materials, aid in producing an integral composite that is useful for making the operative wall of a device. The surfactants act by regulating the surface energy of materials to improve their blending into the composite. This latter material is used for manufacturing devices that maintain their integrity in the environment of use during the agent release period. Generally, the surfactants are amphoteric molecules comprised of a hydrophobic part and a hydrophilic part. The surfactants can be anionic, cationic, nonionic or amphoteric, and they include anionics such as sulfated esters, amides, alcohols, ethers and carboxylic acids; sulfonated aromatic hydrocarbons, aliphatic hydrocarbons, esters and ethers; acylated amino acids and peptides; and metal alkyl phosphates; cationic surfactants such as primary, secondary, tertiary and quaternary alkylammonium salts; acylated polyamines; and salts of heterocyclic amines, arylammonium surfactants such as esters of polyhydric alcohols; alkoxylated amines; polyoxy alkylene; esters and ethers of polyoxyalkylene glycols; alkanolamine fatty acid condensates; tertiary acetylamic glycols; and dialkyl polyoxyalkylene phosphates; and ampholytics such as betamines; and amino acids.

The osmotic pump according to the present invention may also further comprise a second cardio vascular agent. This second agent may be in the form of additional pellets or multiparticulates of a therapeutically effective amount of the agent and a pharmaceutically acceptable carrier within the carrier medium or of an external layer of a pharmaceutically acceptable carrier and a therapeutically effective amount of a cardiovascular agent on the pellets or multiparticulates.

Illustrative of such an osmotic pump according to the present invention are those in which the second cardiovascular agent is selected from alpha receptor blocking agents, alpha and beta receptor blocking agents, angiotensin converting enzyme inhibitors, antianginal agents, anti arrhythmics, antiembolus agents, antihypertensives, beta blocking agents, digitalis, hemorheologic agents, inotropic agents, myocardial infarction prophylaxis, quinidine, cerebral vasodilators, coronary vasodilators, peripheral vasodilators, and vasopressors Exemplifying such an osmotic pump according to the present invention are those in which the cardiovascular agent is selected from angiotensin converting enzyme inhibitors Such angiotensin converting enzyme inhibitors include, without limitation, captopril, enalapril and lisinopril.

The following examples illustrate the preparation of the drug-delivery devices of this invention and their controlled release of one or more therapeutically active ingredients into an environment of use and as such are not to be considered as limiting the invention set forth in the claims appended hereto.

EXAMPLE 1

A multiparticulate formulation for the controlled release of the beneficial agent diltiazem can be prepared by the following procedure.

The following ingredients were placed in a mixing bowl: 100 g of diltiazem L malate, 116 g of sodium bitartrate, 37.5 g of Avicel® and 2.5 g of Methocel® K4M. The powders were mixed using a planetary mixer and 100 ml of water was added to yield a dough. The dough was extruded through 1.2 mm Screen (Luwa® Model EX KS-1 Extruder). The extrudate was left to dry for 5 minutes and then spheronized in a Marumerizer® (Luwa Model QJ-230). The spheres which formed were allowed to dry for 2 days at room temperature and then dried 4 hours at 60° C.

Eighty grams of beads which were retained on an 18 mesh screen but which passed through a 16 mesh screen were coated along with 750 g of sucrose corn starch nonpareils of two screen sizes smaller in a Uniglatt® fluidized bed coater. The coating rate was 30 ml/min with an inlet temperature of 45–50° C. and an outlet temperature of 30–32° C. The atomization air for the spary nozzle was 15 lb/in$^2$ and the beads were fluidized such that the cycle time through the spray area was about 10 seconds. Coating was continued until about 40 micron coat was applied.

The coating solution consisted of 72 g of cellulose acetate butyrate (CAB-381-20), 1000 ml of methylene chloride, 860 ml of methanol, 25.3 g of sorbitol and 50 ml of water. The CAB-381-20 was suspended in the methylene chloride and then 700 ml of methanol added and the polymer dissolved by stirring. The sorbitol was dissolved in the 50 ml of water plus 160 ml of methanol and then added to the polymer solution.

The coated beads were then dried at 45° for 16 hours to remove residual coating solvents.

The release profiles were determined by spectrophotometric measurement of the dissolution media; the absorbance at 270 nm was measured every 5 minutes. The percent diltiazem released was determined using the absorbance reading after the beads had been broken open. FIG. 3 shows the release profiles at 37° C. in pH 1.2 hydrochloric acid solution with 2 g/l of sodium chloride, water, and a 0.05 m phosphate solution at pH 7.5. A standard USP dissolution setup was used with a stirring rate of the paddles being 100 rpm.

EXAMPLE 2

Figure 4:
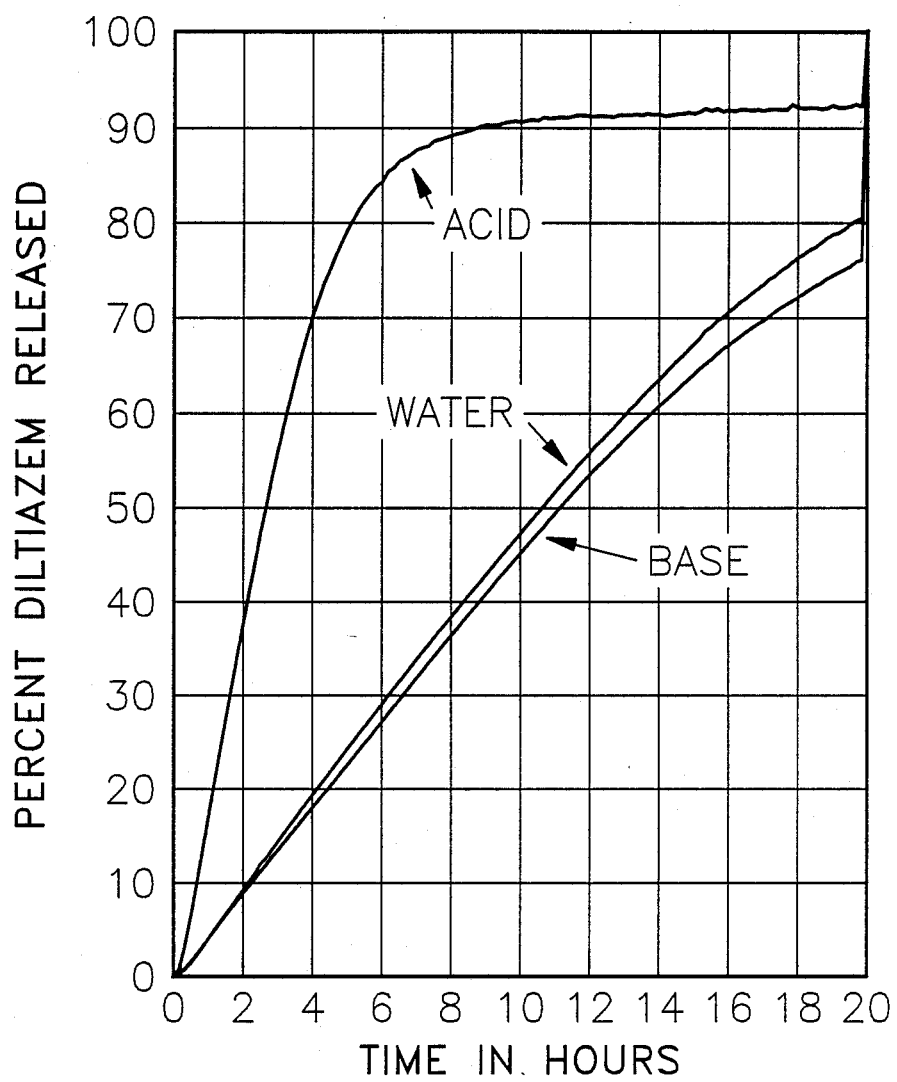
FIG. 4 is the release profile (statistical average of many pumps) of the pumps produced in Example 2.

To show the effect of the sodium bitartrate on drug release a batch of beads were prepared similar to those in Example 1 except no sodium bitartrate was used. The diltiazem L-malate (100 g) was mixed with 25 g of Avicel ® and 1.25 g of Methocel ® K4M in a mixing bowl. Water was added to make a pliable dough and this was extruded and spheronized as described in Example 1. The beads were then dried at 30° C. overnight and then at 60° C. for 3 hours. The same coating solution was used to coat these beads as described in Example 1. The release profiles of the drug from these beads is shown in FIG. 4 in the same release media. The comparison with FIG. 3 shows that the sodium bitartrate is effective in reducing the release rate pH dependency of the coated beads.

EXAMPLE 3

To show how a cardiovascular agent such as enalapril can be combined with this diltiazem L-malate-sodium bitartrate the following example is given. In this example a fast release multiparticulate formulation of enalapril is combined with the controlled release diltiazem L-malate multiparticulates in a hard gelating capsule. The preparation of enalapril beads was accomplished by extrusion and marumerization of the following formulation.

Enalapril Maleate 40 g.
Sodium Bicarbonate 20 g.
Lactose 35 g.
Corn starch 40 g.
Avicel ® RC-581 30 g.
Water g.s.

The enalapril maleate was suspended of water in a 1 l beaker and the sodium bicarbonate was added in small amounts with stirring. As the effervescence subsided, more bicarbonate was added until the total amount had been added. This solution was then added to the remaining powders which had been mixed in a planetary mixer. Sufficient water was then added to form a dough which just began to adhere to the paddle. The dough was broken into chunks and extruded as described in Example 1. The extrudate from the 1.2 mm. screen was collected on a paper lined tray and left to dry for about 5 minutes. The extrudate was then transferred to a Marumerizer ® and spheronized for 5 minutes with plate speed of 1,000 rpm. The beads were emptied onto a paper lined tray and dried at 45° C. for 18 hours.

The release profile was measured using the same procedure as described in Example 1 with absorbance measured at 205 nm. Essentially all of the enalapril was released in 5 minutes.

What is claimed is:

1. A multiparticulate osmotic pump, for the controlled release of diltiazem L-malate to an environment of use, said pump comprising:
   (I) a carrier medium which does not maintain its integrity in the environment of use;
   (II) a multiple of tiny osmotic pump elements each comprising:
   (A) a core which comprises diltiazem L malate and between 80 and 150 percent by weight of sodium bitartrate surrounded by
   (B) a rate controlling water insoluble wall, having a fluid permeability of $6.96 \times 10^{-18}$ to $6.96 \times 10^{\times 14}$ cm$^3$ sec/g and a reflection coefficient of less than 0.5, prepared from:
      (i) a polymer permeable to impermeable to solute and
      (ii) 0.1 to 60% by weight, based on the total weight of (i) and (ii), of at least one pH insensitive pore forming additive dispersed throughout said wall,
   wherein the total amount of diltiazem L-malate in all of the osmotic pump elements is a therapeutically effective amount.

2. An osmotic pump according to claim 1 wherein the total amount of diltiazem L-malate in the core of all the osmotic pump elements is between 30 and 500 mg.

3. An osmotic pump according to claim 1 wherein the total amount of sodium bitartrate in the core of all the osmotic pump elements is between 30 and 500 mg.

4. An osmotic pump according to claim 1, wherein said pore forming additive comprises:
   (a) 0.1 to 50%, by weight, solid additive, based on the total weight of (i) and (ii), and/or
   (b) 0.1 to 40%, by weight, liquid additive, based on the total weight of (i) and (ii), not to exceed a total weight % of pore forming additive of 60%.

5. An osmotic pump according to claim 4 wherein said wall is 10 to 500 microns thick and wall pores are between 10 angstroms and 25 microns in diameter.

6. An osmotic pump according to claim 1, wherein said reflection coefficient is less than 0.1.

7. An osmotic pump according to claim 1, further comprising:
   (c) 0 to 50 parts per 100 parts of (i) and (ii) of plasticizer and flux regulating additives and
   (d) 0 to 40 parts per 100 parts of (i) and (ii), of surfactant additive.

8. An osmotic pump according to claim 1, wherein said water insolube wall is 1 to 1,000 microns thick and wherein 5 to 95% of the resulting wall pores are between 10 angstroms and 100 microns in diameter.

9. An osmotic pump according to claim 1, wherein said polymer is selected from the group consisting of cellulose esters, acylated polysaccharides, polyurethane, polymers of acrylic and methacrylic acid and esters thereof, poly (ortho ester)s, polyacetals and mixtures thereof.

10. An osmotic pump according to claim 9, wherein said polymer is selected from the group consisting of cellulose esters and acylated polysaccharides.

11. An osmotic pump according to claim 9, wherein said polymer is selected from the group consisting of polyurethanes and polymers of acrylic and methacrylic acid and esters thereof.

12. An osmotic pump according to claim 9, wherein said polymer is selected from the group consisting of poly(ortho ester)s and polyacetals.

13. An osmotic pump according to claim 1, wherein said pore forming additive is selected from the group consisting of water, alkali metal salts, alkaline earth metal salts, saccharides, aliphatic polyols, aromatic polyols and mixtures thereof.

14. An osmotic pump according to claim 1, wherein 0.1 to 50%, by weight, of said pore forming additive is used.

15. An osmotic pump according to claim 1, wherein said pH insensitive pore forming additive is selected from the group consisting of polyethylene glycol, sorbitol, glucose and mixtures thereof.

16. An osmotic pump according to claim 1, further comprising:
   additional pellets or multiparticulates of a therapeutically effective amount of a cardiovascular agent and a pharmaceutically acceptable carrier within the carrier medium; or
   an external layer of a pharmaceutically acceptable carrier and a therapeutically effective amount of a cardiovascular agent on the tiny osmotic pump elements.

17. An osmotic pump according to claim 16 wherein the cardiovascular agent is selected from alpha receptor blocking agents, alpha and beta receptor blocking agents, angiotensin converting enzyme inhibitors, antianginal agents, antiarrhythmics, antiembolus agents, antihypertensives, beta blocking agents, digitalis, hemorheologic agents, inotropic agents, myocardial infarction propylaxis, quinidine, cerebral vasodilators, coronary vasodilators, peripheral vasodilators, and vasopressors.

18. An osmotic pump according to claim 17 wherein the cardiovascular agent is selected from angiotensin converting enzyme inhibitors.

19. An osmotic pump according to claim 18 wherein the angiotensin converting enzyme inhibitor is selected from captopril, enalapril and lisinopril.

20. The osmotic pump of claim 1 wherein the carrier medium is solid.

21. The osmotic pump of claim 20 wherein the solid carrier medium is a soluble gelatin capsule or tablet matrix.

22. The osmotic pump of claim 21 wherein the solid carrier medium is a soluble gelatin capsule.